Figure 2:
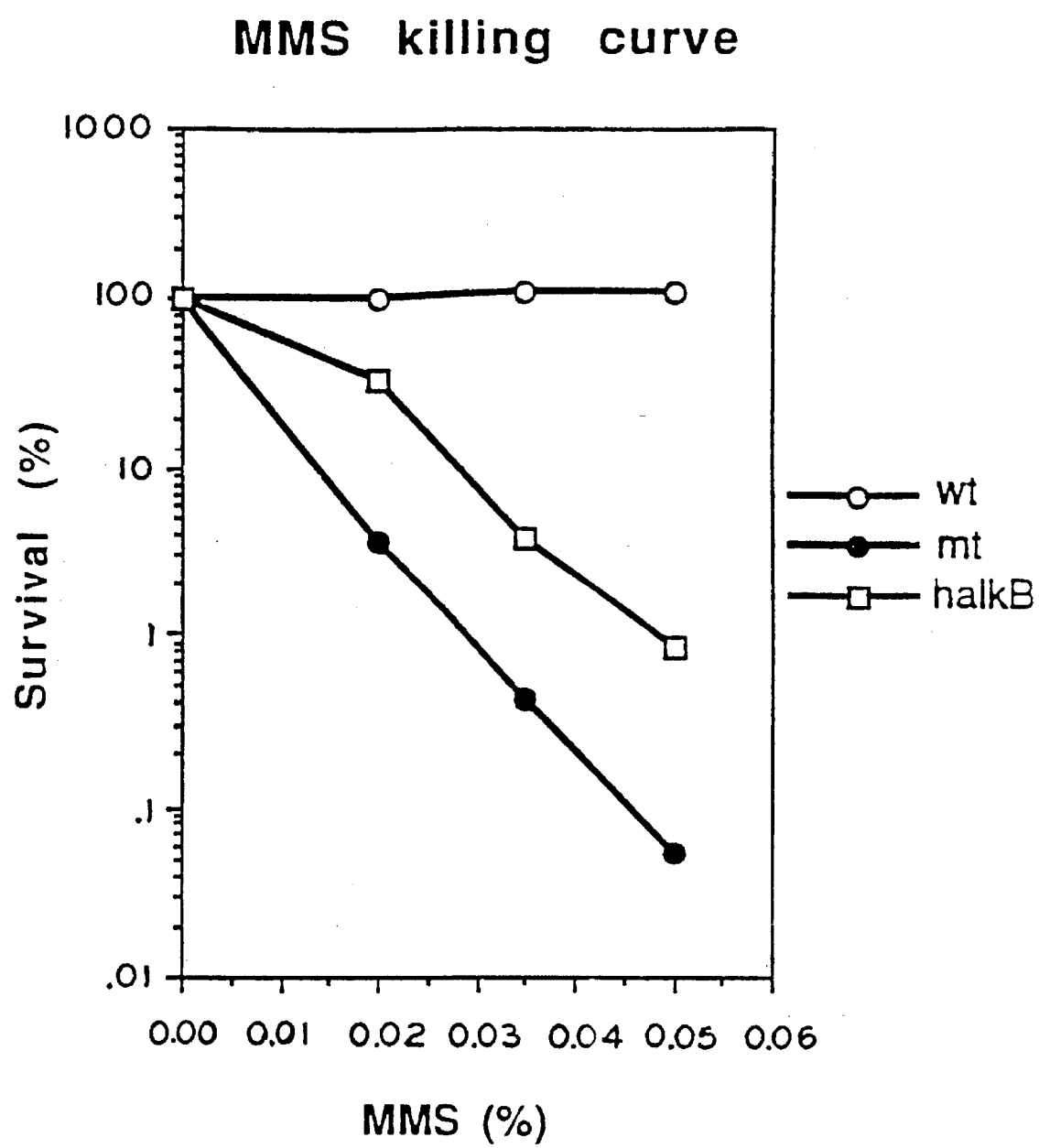

United States Patent [19]
Wei et al.

[11] Patent Number: 5,618,717
[45] Date of Patent: Apr. 8, 1997

[54] DNA ENCODING HUMAN ALKB

[75] Inventors: Ying-Fei Wei, Darnestown; Granger G. Sutton, III, Columbia, both of Md.

[73] Assignee: Human Genome Sciences, Inc., Rockville, Md.

[21] Appl. No.: 463,975

[22] Filed: Jun. 5, 1995

[51] Int. Cl.⁶ .............................. C12N 5/00; C12N 15/00; C12P 21/06; C07H 17/00
[52] U.S. Cl. .................... 435/325; 435/320.1; 435/69.1; 435/183; 435/348; 435/358; 435/365; 435/419; 536/23.2
[58] Field of Search .............................. 435/240.1, 320.1, 435/69.1, 183; 536/23.2

Primary Examiner—Robert A. Wax
Assistant Examiner—K. Cochrane Carlson
Attorney, Agent, or Firm—Elliot M. Olstein

[57] ABSTRACT

A human hABH polypeptide and DNA (RNA) encoding such polypeptide and a procedure for producing such polypeptide by recombinant techniques is disclosed. Also disclosed are methods for utilizing such polypeptide for the treatment of mutations and the treatment of diseases which result from damaged DNA, for example, cancer. Antagonists against such polypeptides and their use as a therapeutic to augment chemotherapy of cancer cells are also disclosed.

16 Claims, 9 Drawing Sheets

FIG. 1A

Polynucleotide and deduced amino acid sequence of hALKB:

```
                    -190              -170              -150
GGGAAGATGGCAGCGGCCGGTGGGCTCTCTGTGGCCGACTCTGGCGACTGAGCCCGGGGAGGAC
----+----|----+----|----+----|----+----|----+----|----+----|----
CCCTTCTACCGTCGCCGGCCACCCGAGACACCGGCTGAGACCGCTGACTCGGGCCCCTCCTG
                 -130              -110               -90

GCCTTTCGGAAACTTTTCCGCTTCTACCGTCAGAGCCCGGGACCGCAGACCTGGA
----+----|----+----|----+----|----+----|----+----|----+----|----
CGGAAAGCCTTTGAAAAGGCGAAGATGGCAGTCTCGGGTCCCGGCCCTGGACCT
        -70               -50               -30

AGGGGTCATCGACTTCTCGGCGGCCCCACGCAGCCCGTGCAAGGGTCCTGGTGCCCAAAAG
----+----|----+----|----+----|----+----|----+----|----+----|----
TCCCCAGTAGCTGAAGAGCCGCGGGTGCGTCGGGCACGTTCCCAGGACCACGGGTTTTC
                  -10                10                30

GTGATCAAATCTCAGCTAAATGTGTCTTCTGTCAGTGAGCAGAATGCATATAGAGCAGGT
----+----|----+----|----+----|----+----|----+----|----+----|----
CACTAGTTTAGAGTCGATTTACACAGAAGACAGTCACTCGTCTTACGTATATCTCGTCCA
             M  C  L  L  S  V  S  R  M  H  I  E  Q  V
       50                70                90

CTTCAGCCCGTCAGCAAGTGGCAAGCCTATGGACTCAAAGGCTATCCTGGGTTTATTTTT
```

FIG. 1B

```
     -----+----+----+----+----+----+----+----+----+----+----+----+
     GAAGTCGGGCAGTCGTTCACCGTTCGGATACCTGAGTTTCCGATAGGACCCAAATAAAAA
      F  S  P  S  A  S  G  K  P  M  D  S  K  A  I  L  G  L  S  L
                      110                 130                 150
                                .                   .
     ATCCCAAACCCCTTCCTCCCCAGGTTACCAGTGGACACTGGGTGAAACAGTGCCTTAAGTT
     -----+----+----+----+----+----+----+----+----+----+----+----+
     TAGGGTTTGGGGAAGGAGGGGTCCAATGGTCACCTGTGACCCACTTTGTCACGGAATTCAA
      S  Q  T  P  S  S  Q  V  T  S  G  H  W  V  K  Q  C  L  K  L
                      170                 190                 210
                                .                   .
     ATATTCCCAGAAACCTAATGTATGTAACCTGGACACACATGTCTAAAGAAGAGACCCA
     -----+----+----+----+----+----+----+----+----+----+----+----+
     TATAAGGGTCTTTGGATTACATACATTGGACCTGTGTGTACAGATTTCTTCTCTGGGT
      Y  S  Q  K  P  N  V  C  N  L  D  T  H  M  S  K  E  E  T  Q
                      230                 250                 270
                                .                   .
     AGATCTGTGGGAACAGAGCAAAGAGTTCCTGAGGTATAAAGAAGCGACTAAACGCAGACC
     -----+----+----+----+----+----+----+----+----+----+----+----+
     TCTAGACACCCTTGTCTCGTTTCTCAAGGACTCCATATTTCTTCGCTGATTTGCCTCTGG
      D  L  W  E  Q  S  K  E  F  L  R  Y  K  E  A  T  K  R  R  P
                      290                 310                 330
                                .                   .
     CCGAAGTTTACTGGAGAAACTGCGTTGGGTGACCGTAGGCTACCATTATAACTGGGACAG
     -----+----+----+----+----+----+----+----+----+----+----+----+
     GGCTTCAAATGACCTCTTTGACGCAACCCACTGGCATCCGATGGTAATATTGACCCTGTC
```

FIG. 1C

```
R  S  L  L  E  K  L  R  W  V  T  V  G  Y  H  Y  N  W  D  S
TAAGAAATACTCAGCAGATCATTACACACCTTTCCCTTCTGACCTGGGTTTCCTCTCAGA
     350              370              390
ATTCTTTATGAGTCGTCTAGTAATGTGTGGAAAGGGAAGACTGGACCCAAAGGAGAGTCT
 K  K  Y  S  A  D  H  Y  T  P  F  P  S  D  L  G  F  L  S  E
     410              430              450

GCAAGTAGCCGCTGCCTGTGGATTTGAGGATTCCGAGCTGAAGCAGGGATCCTGAATTA
CGTTCATCGGCGACGACACCTAAACTCCTAAAGGCTCGACTTCGTCCCTAGGACTTAAT
 Q  V  A  A  A  C  G  S  E  D  S  R  A  E  A  G  I  L  N  Y
     470              490              510

CTACCGCCTGGACTCCACACTGGGAATCCACGTAGACAGATCGGAGCTAGATCACTCCAA
GATGGCGGACCTGAGGTGTGACCCTTAGGTGCATCTGTCTAGACTCGATCTAGTGAGGTT
 Y  R  L  D  S  T  L  G  I  H  V  D  R  S  E  L  D  H  S  K
     530              550              570

ACCCTTGCTGTCATTCAGCTTTGGACAGTCCGCCATCTTTCTCCTGGGTGGTCTTCAAAG
TGGGAACGACAGTAAGTCGAAACCTGTCAGGCGGTAGAAAGAGGACCCACCAGAAGTTTC
 P  L  S  F  S  F  G  Q  S  A  I  F  L  L  G  G  L  Q  R
     590              610              630
```

FIG. 1D

```
GGATGAGGCCCCCCGCCCATGTTTATGCACAGTGGTGACATCATGATAATGTCGGGTTT
----+---------+---------+---------+---------+---------+
CCTACTCCGGGGGGCGGGTACAAATACGTGTCACCACTGTAGTACTATTACAGCCCAAA
 D   E   A   P   P   P   M   F   M   H   S   G   D   I   M   I   M   S   G   S
         650                           670                          690

CAGCCGCCTCTTGAACCACGCAGTCCCTCGTGTCCTTCCAAATCCAGAAGGGGAAGGCCT
----+---------+---------+---------+---------+---------+
GTCGGCGGAGAACTTGGTGCGTCAGGGAGCACAGGAAGGTTTAGGTCTTCCCCTTCCGGA
 S   R   L   N   H   A   V   P   R   V   L   P   N   P   E   G   E   G   L
         710                           730                          750

GCCTCACTGCCTAGAGGCCACCCTCTCCCTGCTCCTGTCCCGAGAGATTCAATGGTAGAGCC
----+---------+---------+---------+---------+---------+
CGGAGTGACGGATCTCCGGTGGAGAGGGACGACAGGAGGGCTCTCTAAGTTACCATCTCGG
 P   H   C   L   E   A   P   L   P   A   V   L   P   R   D   S   M   V   E   P
         770                           790                          810

TTGTTCTATGGAGGACTGGCAGGTGTGTGCCAGCTACTTGAAGACCGCTCGTGTTAACAT
----+---------+---------+---------+---------+---------+
AACAAGATACCTCCTGACCGTCCACACACGGTCGATGAACTTCTGGCGAGCACAATTGTA
 C   S   M   E   D   W   Q   V   C   A   S   Y   L   K   T   A   R   V   N   M
         830                           850                          870

GACTGTCCGACAGGTCCTGGCCACAGAGACCAGAATTTCCCTCTAGAACCCATCGAGGATGA
----+---------+---------+---------+---------+---------+
```

FIG. 1E

```
CTGACAGGCTGTCCAGGACCGGTGTCTGGTCTTAAAGGGAGATCTTGGGTAGCTCCTACT
 T  V  R  Q  V  L  A  T  D  Q  N  F  P  L  E  P  I  E  D  E
            890                   910                    930

AAAAAAGAGACATCAGTACAGAAGTTTCTGCCATCTGGATGACCAGAATAGCGAAGTAA
----+---------+---------+---------+---------+---------+----
TTTTTTCTCTGTAGTCATGTCTTCCAAAGACGGTAGATCTACTGGTCTTATCGCTTCATT
 K  K  R  H  Q  Y  R  R  F  L  P  S  G  *
            950                   970                    990

AACGGGCCAGGATAAACCCTGACAGCTGAGACTTGGAGATCCCATCCTTTTTACTCAGGC
----+---------+---------+---------+---------+---------+----
TTGCCCGGTCCTATTTGGGACTGTCGACTCTGAACCTCTAGGGTAGGAAAAATGAGTCCG
           1010                  1030                   1050

ACCTGCTTACCGTAAATGATCATGTTATTGTGTATTGCCGTGGACTTCAGCACCCAGACA
----+---------+---------+---------+---------+---------+----
TGGACGAATGGCATTTACTAGTACAATAACACATAACGGCACCTGAAGTCGTGGGTCTGT
           1070                  1090                   1110

AGCCAAAAACAGAGACAGGGAAGAACTCATTGTTGATCACACTGTTGCCTTGGAACCCAC
----+---------+---------+---------+---------+---------+----
TCGGTTTTTGTCTCTGTCCCTTCTTGAGTAACAACTAGTGTGACAACGGAACCTTGGGTG
           1130                  1150                   1170

GCAGAAGTAAACTCATCCACTTGCTCAGAGAAGTGTTTGACATGGTCTGTTCCTAGTTA
```

FIG. 1F

```
-----+---------+---------+---------+---------+---------+-------
CGTCTTCATTTGAGTAGGTGAAACGAGTCTCTTCACAAACTGTACCAGACAAGGATCAAT
     1190           1210                    1230
                                        .
CATGTGTTGGCTGTGTAATGTATGTTGAGAAGTCAGTCCAAGGAGGTATGTTCTTCCACAACAG
-----+---------+---------+---------+---------+---------+-------
GTACAACCGACACATTACATATACAACTCTTCAGTCAGGTTCCTCCATACAAGAAGGTGTTGTC
     1250           1270                    1290

CCTTCTCAGCCTCTGCTATTTCCTTTGAGGAAGGTAGAAGTGAGTTTCCATGTTTGCAGA
-----+---------+---------+---------+---------+---------+-------
GGAAGAGTCGGAGACGATAAAGGAAACTCCTTCCATCTTCACTCAAGGTACAAACGTCT
     1310           1330                    1350

GTATTTAAATACCCTCAGATTTTATTAATGAGAAATACAGTACCCCTCCCCTCCACTCCATC
-----+---------+---------+---------+---------+---------+-------
CATAAATTTATGGAGTCTAAAATAATTACTCTTTATGTCATGGGGAGGGAGGTGAGGTAG
     1370           1390                    1410

TGGTAATTTATGGTAAAAATTGTGGTTCTGTGAACCAGCTATTAGTCTCATCTTCTTAACT
-----+---------+---------+---------+---------+---------+-------
ACCATTAAATACCATTTTAACACCAAGACACTTGGTCGATAATCAGAGTAGAAGAATTGA
     1430           1450                    1470

CCCTCAGGCATCATCAAATTCTTTGATCTTCTTCTTCCACCTCTCTGGCTCTCATGGAAGA
-----+---------+---------+---------+---------+---------+-------
```

FIG. 1G

```
GGGAGTCCGTAGTAGTTTAAGAAACTAGAAGAGAAGGTGGAGAGACCGAGAGTACCTTCT
         1490                  1510                  1530
                  .                     .                     .
ATCCTTTACACATGAAAACAATGGAACTGGAAAATCTTGTCTTTTAGAAAAGAAATTAAT
-------+---------+---------+---------+---------+---------+--
TAGGAAATGTGTACTTTTGTTACCTTGACCTTTAGAACAGAAAATCTTTTCTTTAATTA
         1550                  1570                  1590
                  .                     .                     .
CACAACTATCTCTCTTGCCTAAAAGATAAATATAGGTAAACCCAAGGAAAGGGAATTTA
-------+---------+---------+---------+---------+---------+--
GTGTTGATAGAGAACGGATTTTCTATTTATATCCATTTGGGTTCCTTCCCCTTAAAT
         1610                  1630                  1650
                  .                     .                     .
GTTTCTCTACATGTCATTTCGGTCTCCAAACTCCCCTGTTGGCTTTTTAATGCAATTTAA
-------+---------+---------+---------+---------+---------+--
CAAAGAGATGTACAGTAAAGCCAGAGGTTTGAGGGACAACCGAAAAATTACGTTAAAATT
         1670                  1690                  1710
                  .                     .                     .
TTGTTGGAATAAAAAAGTCCCAAGGTGTGTTTTGTTACTGTTTTCTCCATGAATAAACTCA
-------+---------+---------+---------+---------+---------+--
AACAACCTTATTTTTTCAGGGTTCCCACAAAACAATGACAAAAGAGGTACTTATTTGAGT
         1730                  1750
                  .                     .
CTTGATTTTAAAAAAAAAAAAAAAAAAAAAAAAA
-------+---------+-----
GAACTAAAATTTTTTTTTTTTTTTTTTTTTTTTT
```

FIG. 3

```
hALKB   11  IEQVFSPSASGKPMDSKAILGLFLSQTPSSQVTSGHWVKQCLKLYSQK..    58
eAlkB    2  .:ldlfadaepwqeplaagavilrrfafnaaeqlirdindvasqspfrqmvt    51

59  PNVCNLDTHMSKEETQDLWEQSKEFLRYKEATKRRPRSLLEKLRWTVGY   108
        52  pggytmsvamtncghlgwtthrqgyl................yspidp     83

109  HYNWDSKKYSADHYTPFPSDLGFLSEQVAAACGFEDFRAEAGILNYYRLD   158
        84  qtn........kpwpampqsfhnlcgraataagypdfqpdaclinryapg   125

159  STLGIHVDRSELDHSKPLLSFSFGQSAIFLLGGLQRDEAPPPMFMHSGDI   208
       126  aklslhqdkdepdlrapivsvslglpaifqfgglkrndplkrllehgdv    175

209  MINSGFSRLLNHAVPRVLPNPEGEGLPHCLEAPLPAVLPRDSMVEPCSME   258
       176  vvwggesrlfyhgiq..........plkagfhplti..........      201

259  DWQVCASYLKTARVNMTVRQVLATD  283
       202  ........dcrynltfrqagkke    216
```

DNA ENCODING HUMAN ALKB

This invention relates to newly identified polynucleotides, polypeptides encoded by such polynucleotides, the use of such polynucleotides and polypeptides, as well as the production of such polynucleotides and polypeptides. More particularly, the polypeptide of the present invention is human homolog of the bacterial AlkB gene, sometimes hereinafter referred as "hABH". The invention also relates to inhibiting the action of such polypeptides.

Alkylating agents induce DNA damage which may cause either killing of cells or induction of mutation and cancer. Most of such damage is subjected to common cellular DNA repair mechanisms, such as excision repair and postreplication repair (Hanawalt, P. C., et al, Annu. Rev. Biochem., 48:783–836 (1979) and Witkem, Bacteriol. Rev., 40:869–907 (1976)). A repair mechanism is that performed by the human DNA mismatch repair protein.

Certain strain of E. Coli mutants have been found to be specifically sensitive to alkylating agents. Two types of such mutants have been isolated, alkA and tagA (Yamamato, Y., et al., J. Bacteriology, 135:144–152 (1978) and Karran, P., et al., J. Mol. Biol., 40:101–127 (1980)). These genes control the formation of enzymes that catalyze the liberation of certain alkylated bases from damaged DNA (Karran, P., Nature (London), 296:770–773 (1982)). In addition, ada and adc mutants have been isolated which are defective in controlling mechanisms to induce the adaptive response to alkylating agents (Jeggo, P., J. Bacteriol., 139:783–791 (1982)).

The tagA gene has been mapped to an E. Coli chromosome and controls a constitutive enzyme 3-methyladenine-DNA glycosylase I that releases 3-methyladenine from alkylated DNA (Karran, P. et al., Nature (London), 296:770–773 (1982)). The alkA gene has also been mapped and it too controls an inducible enzyme, 3-methyladenine-DNA glycosylase II, which catalyzes the liberation of 3-methyladenine, 3-methylguanine, and 7-methylguanine from the DNA (Evensen, G. and Seeberg, E., Nature (London), 296:773–775 (1982).

Another gene of E. Coli, AlkB, has also been found to control sensitivity to methyl methane sulfonate (MMS). The AlkB gene was located in a region of the chromosome near ada and adc, but is not considered an allele to these genes (Sedgwick, B., J. Bacteriol., 150:984–988 (1982)).

Thus, AlkB resides in a new gene that is near the nalA gene. The AlkB phenotype is different from that of ada, since the AlkB mutant exhibited a normal adaptive response to n-methyl-n'-nitro-n-nitrosoguanidine (Kataoka, H., et al., J. Bact., 153:1301–1307 (1983)). The AlkB gene of E.coli has been found to be responsible for the repair of alkylated DNA (Kondo, H., et al., J. Biol. Chem., 15:1–6, (1986)).

Due to the amino acid sequence between AlkB from E.coli, the present polynucleotide and deduced polypeptide have been putatively identified as a human homolog of the E.coli AlkB protein.

In accordance with one aspect of the present invention, there is provided a novel mature polypeptide which is hABH, as well as fragments, analogs and derivatives thereof. The polypeptide of the present invention is of human origin.

In accordance with another aspect of the present invention, there are provided polynucleotides (DNA or RNA) which encode such polypeptides.

In accordance with yet a further aspect of the present invention, there is provided a process for producing such polypeptide by recombinant techniques.

In accordance with yet a further aspect of the present invention, there is provided a process for utilizing such polypeptide, or polynucleotide encoding such polypeptide for therapeutic purposes, for example, for repairing alkylated DNA and accordingly preventing or treating cell death and cancer.

In accordance with yet a further aspect of the present invention, there are provided antibodies against such polypeptides.

In accordance with yet another aspect of the present invention, there are provided antagonists to such polypeptides, which may be used to inhibit the action of such polypeptides, for example, to prevent this polypeptide from repairing tumor cell DNA during chemotherapy with alkylating agents.

These and other aspects of the present invention should be apparent to those skilled in the art from the teachings herein.

The following drawings are illustrative of embodiments of the invention and are not meant to limit the scope of the invention as encompassed by the claims.

Collectively FIGS. 1A–1G (FIG. 1A is the first portions of the polynucleotide and polypeptide sequences, of SEQ ID NOS: 1 and 2, respectively, FIG. 1B continues with the second sequence portions, and FIGS. 1C–1G continue in like manner to the ends of the same polynucleotide and polypeptide sequences) show the cDNA sequence (SEQ ID NO:1) and corresponding deduced amino acid sequence (SEQ ID NO:2) for hABH. The amino acid sequence shown comprises the putative mature polypeptide. The standard one letter abbreviations for amino acids are used in FIGS. 1A–1G to depict the polypeptide sequence.

FIG. 2 is a schematic illustration of the survival rate of cells in the presence of increasing concentrations of MMS (methyl methane sulfonate). Cells which are wild type for AlkB show no decrease in survival rate as there is an increase in MMS. Mutations (MT) show a dramatic decrease in the survival rate as the concentration of MMS increases. Cells which have the hABH present therein show an increased survival rate as compared to mutant cells.

FIG. 3 illustrates amino acid homology between hABH (top) and AlkB (bottom) from E.coli.

In accordance with an aspect of the present invention, there is provided an isolated nucleic acid (polynucleotide) which encodes for the mature polypeptide having the deduced amino acid sequence of FIG. 1 (SEQ ID NO:2) or for the mature polypeptide encoded by the cDNA of the clone deposited as ATCC Deposit No. 75855 on Aug. 9, 1994.

A polynucleotide encoding a polypeptide of the present invention may be obtained from a human prostate, testis, placenta and heart. The polynucleotide of this invention was discovered in a cDNA library derived from a human synovial sarcoma. It is structurally related to E. Coli AlkB. It contains an open reading frame encoding a protein of 307 amino acid residues. The protein exhibits the highest degree of homology to E.coli AlkB with 23% identity and 52% similarity over a 283 amino acid stretch.

The polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in FIG. 1 (SEQ ID NO:1) or that of the deposited clone or may be a different coding sequence which coding sequence, as a result of the redundancy or degeneracy of the genetic code, encodes the same mature polypeptide as the DNA of FIG. 1 (SEQ ID NO:1) or the deposited cDNA.

The polynucleotide which encodes for the mature polypeptide of FIG. 1 (SEQ ID NO:2) or for the mature polypeptide encoded by the deposited cDNA may include: only the coding sequence for the mature polypeptide; the coding sequence for the mature polypeptide and additional coding sequence such as a leader or secretory sequence or a proprotein sequence; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the deduced amino acid sequence of FIG. 1 (SEQ ID NO:2) or the polypeptide encoded by the cDNA of the deposited clone. The variant of the polynucleotide may be a naturally occurring allelic variant of the polynucleotide or a non-naturally occurring variant of the polynucleotide.

Thus, the present invention includes polynucleotides encoding the same mature polypeptide as shown in FIG. 1 (SEQ ID NO:2) or the same mature polypeptide encoded by the cDNA of the deposited clone as well as variants of such polynucleotides which variants encode for a fragment, derivative or analog of the polypeptide of FIG. 1 or the polypeptide encoded by the cDNA of the deposited clone. Such nucleotide variants include deletion variants, substitution variants and addition or insertion variants.

As hereinabove indicated, the polynucleotide may have a coding sequence which is a naturally occurring allelic variant of the coding sequence shown in FIG. 1 (SEQ ID NO:1) or of the coding sequence of the deposited clone. As known in the art, an allelic variant is an alternate form of a polynucleotide sequence which may have a substitution, deletion or addition of one or more nucleotides, which does not substantially alter the function of the encoded polypeptide.

The present invention also includes polynucleotides, wherein the coding sequence for the mature polypeptide may be fused in the same reading frame to a polynucleotide sequence which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the mature form of the polypeptide. The polynucleotides may also encode for a proprotein which is the mature protein plus additional 5' amino acid residues. A mature protein having a prosequence is a proprotein and is an inactive form of the protein. Once the prosequence is cleaved an active mature protein remains.

Thus, for example, the polynucleotide of the present invention may encode for a mature protein, or for a protein having a prosequence or for a protein having both a prosequence and a presequence (leader sequence).

The polynucleotides of the present invention may also have the coding sequence fused in frame to a marker sequence which allows for purification of the polypeptide of the present invention. The marker sequence may be a hexahistidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The term "gene" means the segment of DNA involved in producing a polypeptide chain; it includes regions preceding and following the coding region (leader and trailer) as well as intervening sequences (introns) between individual coding segments (exons).

Fragments of the full length gene of the present invention may be used as a hybridization probe for a cDNA library to isolate the full length cDNA and to isolate other cDNAs which have a high sequence similarity to the gene or similar biological activity. Probes of this type preferably have at least 30 bases and may contain, for example, 50 or more bases. The probe may also be used to identify a cDNA clone corresponding to a full length transcript and a genomic clone or clones that contain the complete gene including regulatory and promotor regions, exons, and introns. An example of a screen comprises isolating the coding region of the gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

The present invention further relates to polynucleotides which hybridize to the hereinabove-described sequences if there is at least 70%, preferably at least 90%, and more preferably at least 95% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which either retain substantially the same biological function or activity as the mature polypeptide encoded by the cDNAs of FIG. 1 (SEQ ID NO:1) or the deposited cDNA(s).

Alternatively, the polynucleotide may have at least 20 bases, preferably 30 bases, and more preferably at least 50 bases which hybridize to a polynucleotide of the present invention and which has an identity thereto, as hereinabove described, and which may or may not retain activity. For example, such polynucleotides may be employed as probes for the polynucleotide of SEQ ID NO:1, for example, for recovery of the polynucleotide or as a diagnostic probe or as a PCR primer.

Thus, the present invention is directed to polynucleotides having at least a 70% identity, preferably at least 90% and more preferably at least a 95% identity to a polynucleotide which encodes the polypeptide of SEQ ID NO:2 as well as fragments thereof, which fragments have at least 30 bases and preferably at least 50 bases and to polypeptides encoded by such polynucleotides.

The deposit(s) referred to herein will be maintained under the terms of the Budapest Treaty on the International Recognition of the Deposit of Micro-organisms for purposes of Patent Procedure. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted. However, if a patent should issue which is directed to the present invention, upon the issuance of such a patent the deposited strain of ATCC 75855 will be irrevocably and without restriction released to the public, excepting for those restrictions permitted by enforcement of the patent.

The present invention further relates to an hABH polypeptide which has the deduced amino acid sequence of FIG. 1 or which has the amino acid sequence encoded by the deposited cDNA, as well as fragments, analogs and derivatives of such polypeptide.

The terms "fragment," "derivative" and "analog" when referring to the polypeptide of FIG. 1 or that encoded by the deposited cDNA, means a polypeptide which retains essentially the same biological function or activity as such polypeptide. Thus, an analog includes a proprotein which can be activated by cleavage of the proprotein portion to produce an active mature polypeptide.

The polypeptide of the present invention may be a recombinant polypeptide, a natural polypeptide or a synthetic polypeptide, preferably a recombinant polypeptide.

The fragment, derivative or analog of the polypeptide of FIG. 1 or that encoded by the deposited cDNA may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polypeptides of the present invention include the polypeptide of SEQ ID NO:2 (in particular the mature polypeptide) as well as polypeptides which have at least 70% similarity (preferably at least 70% identity) to the polypeptide of SEQ ID NO:2 and more preferably at least 90% similarity (more preferably at least 90% identity) to the polypeptide of SEQ ID NO:2 and still more preferably at least 95% similarity (still more preferably at least 95% identity) to the polypeptide of SEQ ID NO:2 and also include portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the hABH genes. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the *E. coli.* lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli.*

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as *E. coli*, Streptomyces, *Salmonella typhimurium*; fungal cells, such as yeast; insect cells such as Drosophila and Sf9; animal cells such as CHO, COS or Bowes melanoma; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (Qiagen), pBS, pD10, phagescript, psiX174, pbluescript SK, pbsks, pNH8A, pNH16a, pNH18A, pNH46A (Stratagene); ptrc99a, pKK223-3, pKK233-3, pDR540, pRIT5 (Pharmacia). Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are PKK232-8 and PCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation. (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli*, *Bacillus subtilis*, *Salmonella typhimurium* and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., U.S.A.). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The hABH polypeptides can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

The hABH polypeptide of the present invention may be employed to protect against cellular DNA damage as a result of exposure to chemical mutagens. More particularly, the hABH may be used to repair cellular DNA, such as by excision repair, substitution, removing alkylated portion of bases or postreplication repair.

In this manner, the hABH polypeptide of the present invention may be used to treat diseases characterized by abnormal cellular differentiation, for example, cancer. Further, mutated DNA leads to a host of other known and unknown disorders which could be treated with the hABH polypeptide of the present invention.

The present invention also provides a diagnostic assay for detecting mutated hABH genes, which is indicative of a susceptibility to mutation of DNA by various agents, such as chemical mutation. One example of such an assay is the RT-PCR method. For RT-PCR (Reverse Transcriptase Polymerase Chain Reaction), the mRNA encoding hABH is isolated from the total cellular RNA removed from a cell sample. The coding region of the RT-PCR products are then sequenced and compared to the hABH gene to detect mutations. Alternatively, oligonucleotide probes may be prepared which are highly specific for the mRNA to be detected. Such oligonucleotide probes have between 10 and 40 base pairs and preferebly between 10 and 30 base pairs. The oligonucleotide probes may be labelled, for example by radioactivity. The probe is hybridized, for example in situ hybridization, to a cDNA library prepared from total mRNA in a cell sample derived from a host. If there is hybridization, the probe may be removed and the gene to which it hybridizes is sequenced to detect mutations.

The present invention also relates to an assay which demonstrates the biological activity of the hABH gene to protect against the effects of exposure to chemical mutagens and alkylating agents. An example of this type of assay comprises exposing three different groups of E. Coli cells to varying concentrations of an alkylating agent, for example MMS. One cell type is an HK81 strain of E. Coli which is wild-type for the alkB gene. Another cell type is an KH82 strain of E. Coli which is a mutant strain for the alkB gene. The third group is the HK82 strain which has been transfected with a vector containing the hABH gene. A survival percentage of these groups of E. Coli cells is then computed and the results are shown in FIG. 2. It is clear from FIG. 2 that the mutant strain (mt) had the lowest survival rate, while the wild-type (wt) strain had the highest survival rate. The results further show that the hABH gene was able to increase the survival rate of the mutant strain and, therefore, effectively protect against alkylating agents by repairing DNA.

Alternatively, mammalian cells may be employed wherein cells which are wild-type and mutant for the alkB gene may be used. The mutant strain may then be transfected with the hABH gene and percentage of surviving cells calculated. In another embodiment, knock-out mice may be employed wherein the alkB gene has been removed through genetic engineering techniques known to those of skill in the art.

The above-described assay could be used to identify agonist or antagonist compounds. An example of such an assay comprises preparing groups of cells, E. Coli or mammalian, wherein one group is wild-type and the other group is mutant for the alkB gene. The cells are then exposed to the varying amounts of MMS as above. However, in this assay compounds are added to the reaction and the ability of the compound to increase or decrease the survival rate of the mutant strain could then be determined using an assay performed in the absence of any compounds as a control.

Example of potential antagonists to hABH include antibodies, or in some cases an oligonucleotide, which binds to the hABH to eliminate its function. Potential antagonists also include proteins closely related to hABH such that they recognize and bind to the damaged bases of the DNA but do not repair them.

Another potential antagonist includes an antisense construct prepared using antisense technology. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix—see Lee et al., Nucl. Acids Res., 6:3073 (1979); Cooney et al, Science, 241:456 (1988); and Dervan et al., Science, 251: 1360 (1991)), thereby preventing transcription and the production of hABH. The antisense RNA oligonucleotide hybridizes to the mRNA in vivo and blocks translation of the mRNA molecule into the hABH (antisense—Okano, J. Neurochem., 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of hABH.

Potential antagonists also include small molecules which bind to and occupy the effective site of the hABH polypeptide such that it is inaccessible to damaged DNA. Examples of small molecules include but are not limited to small peptides or peptide like molecules.

The antagonists may be employed to specifically target tumor cells and prevent hABH from repairing the DNA of the tumor cell so that the result of chemotherapy with alkylating agents is not offset. However, it is desirable for normal cells to have the alkylated bases repaired by hABH, therefore, the above antagonists are only effective if specifically targeted to tumor cells, or other cells which are the object of chemotherapy. The antagonists may be employed in a composition with a pharmaceutically acceptable carrier, e.g., as hereinafter described.

The polypeptides and agonists and antagonists may be employed in combination with a suitable pharmaceutical carrier. Such compositions comprise a therapeutically effective amount of the polypeptide, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides of the present invention may be employed in conjunction with other therapeutic compounds.

The pharmaceutical compositions may be administered in a convenient manner such as by the oral, topical, intravenous, intraperitoneal, intramuscular, subcutaneous, intranasal or intradermal routes. Pharmaceutical compositions are administered in an amount which is effective for treating and/or prophylaxis of the specific indication. In general, the pharmaceutical compositions will be administered in an amount of at least about 10 μg/kg body weight and in most cases they will be administered in an amount not in excess of about 8 mg/Kg body weight per day. In most cases, the dosage is from about 10 μg/kg to about 1 mg/kg body weight daily, taking into account the routes of administration, symptoms, etc.

The hABH polypeptides and agonists or antagonists may also be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art. For example, cells may be engineered by procedures known in the art by use of a retroviral particle containing RNA encoding a polypeptide of the present invention.

Similarly, cells may be engineered in vivo for expression of a polypeptide in vivo by, for example, procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a polypeptide of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

The vector includes one or more promoters. Suitable promoters which may be employed include, but are not limited to, the retroviral LTR; the SV40 promoter; and the human cytomegalovirus (CMV) promoter described in Miller, et al., *Biotechniques*, Vol. 7, No. 9, 980–990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or hetorologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the β-actin promoter; and human growth hormone promoters. The promoter also may be the native promoter which controls the gene encoding the polypeptide.

The retroviral plasmid vector is employed to transduce packaging cell lines to form producer cell lines. Examples of packaging cells which may be transfected include, but are not limited to, the PE501, PA317, ψ-2, ψ-AM, PA12, T19-14X, VT-19-17-H2, ψCRE, ψCRIP, GP+E-86, GP+envAm12, and DAN cell lines as described in Miller, *Human Gene Therapy*, Vol. 1, pgs. 5–14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

This invention is also related to the use of the gene of the present invention as a diagnostic. Detection of a mutated form of the gene will allow a diagnosis of a disease or a susceptibility to a disease which results from underexpression of hABH.

Individuals carrying mutations in the gene of the present invention may be detected at the DNA level by a variety of techniques. Nucleic acids for diagnosis may be obtained from a patient's cells, including but not limited to blood, urine, saliva, tissue biopsy and autopsy material. The genomic DNA may be used directly for detection or may be amplified enzymatically by using PCR (Saiki et al., Nature, 324:163–166 (1986)) prior to analysis. RNA or cDNA may also be used for the same purpose. As an example, PCR primers complementary to the nucleic acid encoding hABH can be used to identify and analyze mutations. For example, deletions and insertions can be detected by a change in size of the amplified product in comparison to the normal genotype. Point mutations can be identified by hybridizing amplified DNA to radiolabeled RNA or alternatively, radiolabeled antisense DNA sequences. Perfectly matched sequences can be distinguished from mismatched duplexes by RNase A digestion or by differences in melting temperatures.

Sequence differences between the reference gene and genes having mutations may be revealed by the direct DNA sequencing method. In addition, cloned DNA segments may be employed as probes to detect specific DNA segments. The sensitivity of this method is greatly enhanced when combined with PCR. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., Science, 230:1242 (1985)).

Sequence changes at specific locations may also be revealed by nuclease protection assays, such as RNase and S1 protection or the chemical cleavage method (e.g., Cotton et al., PNAS, U.S.A., 85:4397–4401 (1985)).

Thus, the detection of a specific DNA sequence may be achieved by methods such as hybridization, RNase protection, chemical cleavage, direct DNA sequencing or the use of restriction enzymes, (e.g., Restriction Fragment Length Polymorphisms (RFLP)) and Southern blotting of genomic DNA.

In addition to more conventional gel-electrophoresis and DNA sequencing, mutations can also be detected by in situ analysis.

The present invention also relates to a diagnostic assay for detecting altered levels of the polypeptide of the present invention in various tissues. Assays used to detect levels of the polypeptide of the present invention in a sample derived from a host are well-known to those of skill in the art and include radioimmunoassays, competitive-binding assays, Western Blot analysis and preferably an ELISA assay. An ELISA assay initially comprises preparing an antibody specific to the hABH antigen, preferably a monoclonal antibody. In addition a reporter antibody is prepared against the monoclonal antibody. To the reporter antibody is attached a detectable reagent such as radioactivity, fluorescence or in this example a horseradish peroxidase enzyme. A sample is now removed from a host and incubated on a solid support, e.g. a polystyrene dish, that binds the proteins in the sample. Any free protein binding sites on the dish are then covered by incubating with a non-specific protein such as bovine serum albumin. Next, the monoclonal antibody is incubated in the dish during which time the monoclonal antibodies attached to any of the polypeptide of the present invention attached to the polystyrene dish. All unbound monoclonal antibody is washed out with buffer. The reporter antibody linked to horseradish peroxidase is now placed in the dish resulting in binding of the reporter antibody to any monoclonal antibody bound to the polypeptide of the present invention. Unattached reporter antibody is then washed out. Peroxidase substrates are then added to the dish and the amount of color developed in a given time period is a measurement of the amount of the polypeptide of the present invention present in a given volume of patient sample when compared against a standard curve.

A competition assay may be employed wherein antibodies specific to the polypeptide of the present invention are attached to a solid support and labeled hABH and a sample derived from the host are passed over the solid support and the amount of label detected attached to the solid support can be correlated to a quantity of the polypeptide of the present invention in the sample.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA having at least 50 or 60 bases. For a review of this technique, see Verma et al., Human Chromosomes: a Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 µg of plasmid or DNA fragment is used with about 2 units of enzyme in about 20 µl of buffer solution. For the purpose of isolating DNA fragments for plasmid construction, typically 5 to 50 µg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units to T4 DNA ligase ("ligase") per 0.5 µg of approximately equimolar amounts of the DNA fragments to be ligated.

Unless otherwise stated, transformation was performed as described in the method of Graham, F. and Van der Eb, A., Virology, 52:456–457 (1973).

EXAMPLE 1

Bacterial Expression and Functional Complementation of hABH

The DNA sequence encoding for hABH, ATCC #75855, is initially amplified using PCR oligonucleotide primers corresponding to the 5' and 3' sequences of the hABH protein. The 5' oligonucleotide primer has the sequence 5' GCGCGTCGACATGTGTCTTCTGTCAGTG (SEQ ID NO:3) contains a SalI restriction enzyme site (underlined) followed by 18 nucleotides of hABH coding sequence starting from the presumed N-terminal amino acid of the protein codon. The 3' primer has the sequence 5' GCG-CAAGCTTTCATCCAGATGGCAGAAACC 3' (SEQ ID NO:4) contains complementary sequences to a HindIII site (underlined) and is followed by 20 nucleotides of hABH. The restriction enzyme sites correspond to the restriction enzyme sites on the bacterial expression vector pQE-9 (Qiagen, Inc. 9259 Eton Avenue, Chatsworth, Calif., 91311). pQE-9 encodes antibiotic resistance (Amp'), a bacterial origin of replication (ori), an IPTG-regulatable promoter operator (P/O), a ribosome binding site (RBS), a 6-His tag and restriction enzyme sites. pQE-9 was then digested with SalI and HindIII. The amplified sequences were ligated into pQE-9 and were inserted in frame with the sequence encoding for the histidine tag and the RBS. The ligation mixture was then used to transform E. coli mutant strain HK82 by the procedure described in Sambrook, J. et al., Molecular Cloning: A Laboratory Manual, Cold Spring Laboratory Press, (1989). Transformants are identified by their ability to grow on LB plates and ampicillin resistant colonies were selected. Plasmid DNA was isolated and confirmed by restriction analysis.

The AlkB mutant strain of HK82 was then examined for its ability to complement an AlkB mutant. Wild-type E. Coli strain HK81 harboring the pQE-9 vector and mutant E. Coli strain HK82 containing the vector pQE-9hABH were grown to 2×10⁸ cells per milliliter in LB ampicillin medium at 37 degrees C. The cells were then diluted with M9 salts, and plated on LB ampicillin plates containing 0, 0,001, 0.02, and 0.03% of MMS. The plates were incubated at 37 degree C. overnight. The results are depicted in FIG. 2.

EXAMPLE 2

Expression of Recombinant hABH in COS Cells

The expression of plasmid, hABH HA is derived from a vector pcDNAI/Amp (Invitrogen) containing: 1) SV40 origin of replication, 2) ampicillin resistance gene, 3) E.coli replication origin, 4) CMV promoter followed by a polylinker region, a SV40 intron and polyadenylation site. A DNA fragment encoding the entire hABH precursor and a HA tag fused in frame to its 3' end was cloned into the polylinker region of the vector, therefore, the recombinant protein expression is directed under the CMV promoter. The HA tag correspond to an epitope derived from the influenza hemagglutinin protein as previously described (I. Wilson, H. Niman, R. Heighten, A Cherenson, M. Connolly, and R. Lerner, 1984, Cell 37, 767). The infusion of HA tag to our target protein allows easy detection of the recombinant protein with an antibody that recognizes the HA epitope.

The plasmid construction strategy is described as follows:

The DNA sequence encoding for hABH, ATCC #75855, was constructed by PCR on the original EST cloned using two primers: the 5' primer 5' GCGCAAGCTTATGTGTCT-TCTGTCAGTG 3' (SEQ ID NO:5) contains a HindIII site (underlined) followed by 18 nucleotides of hABH coding sequence starting from the initiation codon; the 3' primer sequence 5'GCGCGAATTCTCAAGCG TAGTCTGG-GACGTCGTATGGGTATCCAGATGGCAGAAACC 3' (SEQ ID NO:6) contains an EcoRI site, complementary sequences to a translation stop codon, HA tag and the last 17 nucleotides of the hABH coding sequence (not including the stop codon). Therefore, the PCR product contains a HindIII site, hABH coding sequence followed by HA tag fused in frame, a translation termination stop codon next to the HAtag, and an EcoRI site. The PCR amplified DNA fragment and the vector, pcDNAI/Amp, were digested with HindIII and EcoRI restriction enzyme and ligated. The ligation mixture was transformed into E. coli strain SURE (available from Stratagene Cloning Systems, 11099 North Torrey Pines Road, La Jolla, Calif. 92037) the transformed culture was plated on ampicillin media plates and resistant colonies were selected. Plasmid DNA was isolated from transformants and examined by restriction analysis for the presence of the correct fragment. For expression of the recombinant hABH, COS cells were transfected with the expression vector by DEAE-DEXTRAN method. (J. Sambrook, E. Fritsch, T. Maniatis, Molecular Cloning: A Laboratory Manual, Cold Spring Laboratory Press, (1989)). The expression of the hABH HA protein was detected by radiolabelling and immunoprecipitation method. (E. Harlow, D. Lane, Antibodies: A Laboratory Manual, Cold Spring Harbor Laboratory Press, (1988)). Cells were labelled for 8 hours with ³⁵S-cysteine two days post transfection. Culture media were then collected and cells were lysed with detergent (RIPA buffer (150 mM NaCl, 1% NP-40, 0.1% SDS, 1% NP-40, 0.5% DOC, 50 mM Tris, pH 7.5). (Wilson, I. et al., Id. 37:767 (1984)). Both cell lysate and culture media were precipitated with a HA specific monoclonal antibody. Proteins precipitated were analyzed on 15% SDS-PAGE gels.

EXAMPLE 3

Expression Pattern of hABH in Human Tissue

Northern blot analysis was carried out to examine the levels of expression of hABH in human tissues. Total cellular RNA samples were isolated with RNAzol™ B system (Biotecx Laboratories, Inc. 6023 South Loop East, Houston, Tex. 77033). About 10 µg of total RNA isolated from each human tissue specified was separated on 1% agarose gel and blotted onto a nylon filter. (Sambrook, Fritsch, and Maniatis, Molecular Cloning, Cold Spring Harbor Press, (1989)). The labeling reaction was done according to the Stratagene Prime-It kit with 50 ng DNA fragment. The labeled DNA was purified with a Select-G-50 column. (5 Prime—3 Prime, Inc. 5603 Arapahoe Road, Boulder, Colo. 80303). The filter was then hybridized with radioactive labeled full length hABH gene at 1,000,000 cpm/ml in 0.5M $NaPO_4$, pH 7.4 and 7% SDS overnight at 65° C. After wash twice at room temperature and twice at 60° C. with 0.5×SSC, 0.1% SDS, the filter was then exposed at −70° C. overnight with an intensifying screen. The message RNA for hABH is abundant in thymus, testis, gall bladder, liver, prostate, heart and placenta.

EXAMPLE 4

Expression via Gene Therapy

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin, is added. This is then incubated at 37° C. for approximately one week. At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al, DNA, 7:219–25 (1988) flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention is amplified using PCR primers which correspond to the 5' and 3' end sequences respectively. The 5' primer containing an EcoRI site and the 3' primer $further includes a HindIII site. Equal quantities of the Moloney murine sarcoma virus linear backbone and the amplified $EcoRI and HindIII fragment are added together, in the presence of T4 DNA ligase. The resulting mixture is maintained under conditions appropriate for ligation of the two fragments. The ligation mixture is used to transform bacteria HB101, which are then plated onto agar-containing kanamycin for the purpose of confirming that the vector had the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells are transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product.

Numerous modifications and variations of the present invention are possible in light of the above teachings and, therefore, within the scope of the appended claims, the invention may be practiced otherwise than as particularly described.

What is claimed is:

1. An isolated polynucleotide comprising a polynucleotide having at least 95% identity to a member selected from the group consisting of:
   (a) a polynucleotide encoding a polypeptide comprising amino acid 2 to 307 of SEQ ID NO:2;
   (b) the complement of (a).

2. The isolated polynucleotide of claim 1 wherein said member is (a).

3. The isolated polynucleotide of claim 1 wherein said polynucleotide encodes a polypeptide comprising amino acid 1 to 307 of SEQ ID NO:2.

4. The isolated polynucleotide of claim 1 comprising nucleotides 200 to 1953 of SEQ ID NO:1.

5. The isolated polynucleotide of claim 1 comprising a polynucleotide sequence identical to the polynucleotide sequence of SEQ ID N0:1.

6. The isolated polynucleotide of claim 1, wherein the polynucleotide is DNA.

7. The isolated polynucleotide of claim 1, wherein said polynucleotide is RNA.

8. A method of making a recombinant vector comprising inserting the isolated polynucleotide of claim 2 into a vector, wherein said polynucleotide is DNA.

9. A recombinant vector comprising the polynucleotide of claim 2, wherein said polynucleotide is DNA.

10. A recombinant host cell comprising the polynucleotide of claim 2, wherein said polynucleotide is DNA.

11. A method for producing a polypeptide comprising expressing from the recombinant cell of claim 10 the polypeptide encoded by said polynucleotide.

12. An isolated polynucleotide comprising a polynucleotide having at least a 95% identity to a member selected from the group consisting of:
   (a) a polynucleotide encoding the same mature polypeptide encoded by the human cDNA in ATCC Deposit No. 75855, and
   (b) the complement of (a).

13. The isolated polynucleotide of claim 12, wherein the member is (a).

14. The isolated polynucleotide of claim 12, wherein the member is (b).

15. The isolated polynucleotide of claim 12 comprising a polynucleotide which encodes for the same mature polypeptide encoded by the human cDNA in ATCC Deposit No. 75855.

16. The isolated polynucleotide of claim 12 wherein said polynucleotide comprises DNA identical to the coding portion of the human cDNA in ATCC Deposit No. 75855 which encodes a mature polypeptide.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
( A ) LENGTH: 1953 BASE PAIRS
( B ) TYPE: NUCLEIC ACID
( C ) STRANDEDNESS: SINGLE
( D ) TOPOLOGY: LINEAR ( i i ) MOLECULE TYPE: cDNA ( x i ) SEQUENCE DESCRIPTION: SEQ ID NO:1:

| | | | | | | |
|---|---|---|---|---|---|---|
| GGGAAGATGG | CAGCGGCCGT | GGGCTCTGTG | GCGACTCTGG | CGACTGAGCC | CGGGGAGGAC | 60 |
| GCCTTTCGGA | AACTTTTCCG | CTTCTACCGT | CAGAGCCGGG | CCCGGGACCG | CAGACCTGGA | 120 |
| AGGGGTCATC | GACTTCTCGG | CGGCCCACGC | AGCCCGTGCA | AGGGTCCTGG | TGCCCAAAAG | 180 |
| GTGATCAAAT | CTCAGCTAAA | TGTGTCTTCT | GTCAGTGAGC | AGAATGCATA | TAGAGCAGGT | 240 |
| CTTCAGCCCG | TCAGCAAGTG | GCAAGCCTAT | GGACTCAAAG | GCTATCCTGG | GTTTATTTTT | 300 |
| ATCCCAAACC | CCTTCCTCCC | AGGTTACCAG | TGGACACTGG | GTGAAACAGT | GCCTTAAGTT | 360 |
| ATATTCCCAG | AAACCTAATG | TATGTAACCT | GGACACACAC | ATGTCTAAAG | AAGAGACCCA | 420 |
| AGATCTGTGG | GAACAGAGCA | AAGAGTTCCT | GAGGTATAAA | GAAGCGACTA | AACGGAGACC | 480 |
| CCGAAGTTTA | CTGGAGAAAC | TGCGTTGGGT | GACCGTAGGC | TACCATTATA | ACTGGGACAG | 540 |
| TAAGAAATAC | TCAGCAGATC | ATTACACACC | TTTCCCTTCT | GACCTGGGTT | TCCTCTCAGA | 600 |
| GCAAGTAGCC | GCTGCCTGTG | GATTTGAGGA | TTTCCGAGCT | GAAGCAGGGA | TCCTGAATTA | 660 |
| CTACCGCCTG | GACTCCACAC | TGGGAATCCA | CGTAGACAGA | TCTGAGCTAG | ATCACTCCAA | 720 |
| ACCCTTGCTG | TCATTCAGCT | TTGGACAGTC | CGCCATCTTT | CTCCTGGGTG | GTCTTCAAAG | 780 |
| GGATGAGGCC | CCCCCGCCCA | TGTTTATGCA | CAGTGGTGAC | ATCATGATAA | TGTCGGGTTT | 840 |
| CAGCCGCCTC | TTGAACCACG | CAGTCCCTCG | TGTCCTTCCA | AATCCAGAAG | GGGAAGGCCT | 900 |
| GCCTCACTGC | CTAGAGGCAC | CTCTCCCTGC | TGTCCTCCCG | AGAGATTCAA | TGGTAGAGCC | 960 |
| TTGTTCTATG | GAGGACTGGC | AGGTGTGTGC | CAGCTACTTG | AAGACCGCTC | GTGTTAACAT | 1020 |
| GACTGTCCGA | CAGGTCCTGG | CCACAGACCA | GAATTTCCCT | CTAGAACCCA | TCGAGGATGA | 1080 |
| AAAAAAGAGA | CATCAGTACA | GAAGGTTTCT | GCCATCTGGA | TGACCAGAAT | AGCGAAGTAA | 1140 |
| AACGGGCCAG | GATAAACCCT | GACAGCTGAG | ACTTGGAGAT | CCCATCCTTT | TTACTCAGGC | 1200 |
| ACCTGCTTAC | CGTAAATGAT | CATGTTATTG | TGTATTGCCG | TGGACTTCAG | CACCCAGACA | 1260 |
| AGCCAAAAAC | AGAGACAGGG | AAGAACTCAT | TGTTGATCAC | ACTGTTGCCT | TGGAACCCAC | 1320 |

```
GCAGAAGTAA ACTCATCCAC TTTGCTCAGA GAAGTGTTTG ACATGGTCTG TTCCTAGTTA      1380

CATGTTGGCT GTAATGTATG TTGAGAAGTC AGTCCAAGGA GGTATGTTCT TCCACAACAG      1440

CCTTCTCAGC CTCTGCTATT TCCTTTGAGG AAGGTAGAAG TGAGTTTCCA TGTTTGCAGA      1500

GTATTTAAAT ACCTCAGATT TTATTAATGA GAAATACAGT ACCCCTCCCT CCACTCCATC      1560

TGGTAATTTA TGGTAAAATT GTGGTTCTGT GAACCAGCTA TTAGTCTCAT CTTCTTAACT      1620

CCCTCAGGCA TCATCAAATT CTTTGATCTT CTCTTCCACC TCTCTGGCTC TCATGGAAGA      1680

ATCCTTTACA CATGAAAACA ATGGAACTGG AAAATCTTGT CTTTTAGAAA AGAAATTAAT      1740

CACAACTATC TCTCTTGCCT AAAAGATAAA TATAGGTAAA CCCAAGGAAA GGGGAATTTA      1800

GTTTCTCTAC ATGTCATTTC GGTCTCCAAA CTCCCTGTTG CTTTTTAAT GCAATTTTAA       1860

TTGTTGGAAT AAAAAAGTCC CAAGGGTGTT TTGTTACTGT TTTCTCCATG AATAAACTCA      1920

CTTGATTTTA AAAAAAAAAA AAAAAAAAA AAA                                    1953
```

( 2 ) INFORMATION FOR SEQ ID NO:2:

( i ) SEQUENCE CHARACTERISTICS:
        ( A ) LENGTH: 307 AMINO ACIDS
        ( B ) TYPE: AMINO ACID
        ( C ) STRANDEDNESS:
        ( D ) TOPOLOGY: LINEAR ( i i ) MOLECULE TYPE: PROTEIN ( x i ) SEQUENCE DESCRIPTION: SEQ ID NO:2:

```
Met Cys Leu Leu Ser Val Ser Arg Met His Ile Glu Gln Val Phe
              5                  10                  15

Ser Pro Ser Ala Ser Gly Lys Pro Met Asp Ser Lys Ala Ile Leu
              20                 25                  30

Gly Leu Phe Leu Ser Gln Thr Pro Ser Ser Gln Val Thr Ser Gly
              35                 40                  45

His Trp Val Lys Gln Cys Leu Lys Leu Tyr Ser Gln Lys Pro Asn
              50                 55                  60

Val Cys Asn Leu Asp Thr His Met Ser Lys Glu Thr Gln Asp
              65                 70                  75

Leu Trp Glu Gln Ser Lys Glu Phe Leu Arg Tyr Lys Glu Ala Thr
              80                 85                  90

Lys Arg Arg Pro Arg Ser Leu Leu Glu Lys Leu Arg Trp Val Thr
              95                 100                 105

Val Gly Tyr His Tyr Asn Trp Asp Ser Lys Lys Tyr Ser Ala Asp
              110                115                 120

His Tyr Thr Pro Phe Pro Ser Asp Leu Gly Phe Leu Ser Glu Gln
              125                130                 135

Val Ala Ala Ala Cys Gly Phe Glu Asp Phe Arg Ala Glu Ala Gly
              140                145                 150

Ile Leu Asn Tyr Tyr Arg Leu Asp Ser Thr Leu Gly Ile His Val
              155                160                 165

Asp Arg Ser Glu Leu Asp His Ser Lys Pro Leu Leu Ser Phe Ser
              170                175                 180

Phe Gly Gln Ser Ala Ile Phe Leu Leu Gly Gly Leu Gln Arg Asp
              185                190                 195

Glu Ala Pro Pro Pro Met Phe Met His Ser Gly Asp Ile Met Ile
              200                205                 210

Met Ser Gly Phe Ser Arg Leu Leu Asn His Ala Val Pro Arg Val
              215                220                 225
```

```
Leu  Pro  Asn  Pro  Glu  Gly  Glu  Gly  Leu  Pro  His  Cys  Leu  Glu  Ala
               230                      235                          240

Pro  Leu  Pro  Ala  Val  Leu  Pro  Arg  Asp  Ser  Met  Val  Glu  Pro  Cys
               245                      250                          255

Ser  Met  Glu  Asp  Trp  Gln  Val  Cys  Ala  Ser  Tyr  Leu  Lys  Thr  Ala
               260                      265                          270

Arg  Val  Asn  Met  Thr  Val  Arg  Gln  Val  Leu  Ala  Thr  Asp  Gln  Asn
               275                      280                          285

Phe  Pro  Leu  Glu  Pro  Ile  Glu  Asp  Glu  Lys  Lys  Arg  His  Gln  Tyr
               290                      295                          300

Arg  Arg  Phe  Leu  Pro  Ser  Gly
               305
```

( 2 ) INFORMATION FOR SEQ ID NO:3:

( i ) SEQUENCE CHARACTERISTICS:
        ( A ) LENGTH: 28 BASE PAIRS
        ( B ) TYPE: NUCLEIC ACID
        ( C ) STRANDEDNESS: SINGLE
        ( D ) TOPOLOGY: LINEAR ( i i ) MOLECULE TYPE: Oligonucleotide ( x i ) SEQUENCE DESCRIPTION: SEQ ID NO:3:

GCGCGTCGAC ATGTGTCTTC TGTCAGTG                                    28

( 2 ) INFORMATION FOR SEQ ID NO:4:

( i ) SEQUENCE CHARACTERISTICS:
        ( A ) LENGTH: 30 BASE PAIRS
        ( B ) TYPE: NUCLEIC ACID
        ( C ) STRANDEDNESS: SINGLE
        ( D ) TOPOLOGY: LINEAR ( i i ) MOLECULE TYPE: Oligonucleotide ( x i ) SEQUENCE DESCRIPTION: SEQ ID NO:4:

GCGCAAGCTT TCATCCAGAT GGCAGAAACC                                  30

( 2 ) INFORMATION FOR SEQ ID NO:5:

( i ) SEQUENCE CHARACTERISTICS:
        ( A ) LENGTH: 28 BASE PAIRS
        ( B ) TYPE: NUCLEIC ACID
        ( C ) STRANDEDNESS: SINGLE
        ( D ) TOPOLOGY: LINEAR ( i i ) MOLECULE TYPE: Oligonucleotide ( x i ) SEQUENCE DESCRIPTION: SEQ ID NO:5:

GCGCAAGCTT ATGTGTCTTC TGTCAGTG                                    28

( 2 ) INFORMATION FOR SEQ ID NO:6:

( i ) SEQUENCE CHARACTERISTICS:
        ( A ) LENGTH: 57 BASE PAIRS
        ( B ) TYPE: NUCLEIC ACID
        ( C ) STRANDEDNESS: SINGLE
        ( D ) TOPOLOGY: LINEAR ( i i ) MOLECULE TYPE: Oligonucleotide ( x i ) SEQUENCE DESCRIPTION: SEQ ID NO:6:

GCGCGAATTC TCAAGCGTAG TCTGGGACGT CGTATGGGTA TCCAGATGGC AGAAACC    57